United States Patent [19]

Wojtowicz

[11] 4,007,182
[45] Feb. 8, 1977

[54] PROCESS FOR PRODUCING TRICHLOROISOCYANURIC ACID FROM SELECTED SYMMETRICAL TRIAZINES

[75] Inventor: John A. Wojtowicz, Cheshire, Conn.

[73] Assignee: Olin Corporation, New Haven, Conn.

[22] Filed: Feb. 24, 1976

[21] Appl. No.: 660,962

[52] U.S. Cl. .................................... 260/248 C
[51] Int. Cl.$^2$ ..................... C07D 251/36
[58] Field of Search ........................ 260/248 C

[56] References Cited

UNITED STATES PATENTS

| | | | |
|---|---|---|---|
| 3,806,507 | 4/1974 | Sawhill | 260/248 |
| 3,835,134 | 9/1974 | Schiessl et al. | 260/248 |

Primary Examiner—John M. Ford
Attorney, Agent, or Firm—James B. Haglind; Donald F. Clements; Thomas P. O'Day

[57] ABSTRACT

Trichloroisocyanuric acid is produced by the reaction of a symmetrical triazine compound selected from the group consisting of ammelide, chlorosubstituted ammelide, an alkali metal salt of ammelide, ammeline, chlorosubstituted ammeline, an alkali metal salt of ammeline with hypochlorous acid. The number of moles of hypochlorous acid reacted per mole of the symmetrical triazine compound is at least $X + 2Y$ where $X$ represents the number of hydrogen and alkali metal atoms present in the triazine compound and $Y$ represents the number of nitrogen atoms in the triazine compound which are replaced by oxygen atoms.

13 Claims, No Drawings

PROCESS FOR PRODUCING TRICHLOROISOCYANURIC ACID FROM SELECTED SYMMETRICAL TRIAZINES

This invention relates to a process for the production of trichloroisocyanuric acid from selected symmetrical triazine compounds. Trichloroisocyanuric acid is a commercial product used in washing, bleaching and sanitizing applications.

It is known to react chlorine gas with amides or imides of cyanuric acid such as ammelide or ammeline to produce chlorinated ammelide and chlorinated ammeline as described in U.S. Pat. No. 2,184,886, issued to Muskat et al. These chlorinated compounds, while containing considerable amounts of active chlorine, have found little use and are not produced commercially.

Now it has been found that symmetrical triazine compounds such as ammelide and ammeline can be converted to trichloroisocyanuric acid, a well known commercial product.

An object of the present invention is a process for preparing trichloroisocyanuric acid from selected symmetrical triazine compounds.

Another object of the present invention is a process for preparing trichloroisocyanuric acid from cyanuric acid containing selected symmetrical triazine compounds as impurities.

These and other objects of the present invention will be apparent from the following detailed description of the invention.

Briefly, the process of the present invention for producing trichloroisocyanuric acid comprises reacting a symmetrical triazine compound selected from the group consisting of ammeline, chlorosubstituted ammeline, alkali metal salts of ammeline, ammelide, chlorosubstituted ammelide, alkali metal salts of ammelide and mixtures thereof, with hypochlorous acids to form a reaction mixture containing said trichloroisocyanuric acid wherein the moles of hypochlorous acid reacted are at least $X + 2Y$, where $X$ represents the number of hydrogen and alkali metal atoms present in the symmetrical triazine compound and $Y$ represents the number of nitrogen atoms which are replaced by an oxygen atom.

More in detail, symmetrical triazine compounds such as ammelide or ammeline are known compounds which can be synthesized by known methods. Ammeline, is prepared for example, by the reaction of cyanoguanidine with urea, ammonia, or potassium cyanate while ammelide can be synthesized, for example, by the pressurized reaction of dicyandiamide with $CO_2$.

Both compounds also are often present as impurities in cyanuric acid which has been prepared by the pyrolysis of urea.

In addition to ammeline and ammelide, chlorosubstituted derivatives such as dichloroammeline, monochloro- or trichloroammelide may be used in the process of the present invention as well as alkali metal salts of ammelide or ammeline.

Suitable as alkali metals in the alkali metal salts of ammelide or ammeline are lithium, sodium, potassium, cesium, and rubidium. For economic reasons, sodium and potassium are preferred alkali metals.

The hypochlorous acid employed can be made by several methods including the chlorination of an aqueous solution of an alkali metal or alkaline earth hypochlorite, the chlorination of aqueous solution of alkali metal or alkaline earth carbonates or bi-carbonates, or the reaction of an aqueous acid stronger than hypochlorous acid, for example, sulfuric, nitric, phosphoric or hydrochloric acid, with an alkali metal or alkaline earth metal hypochlorite. In addition, solutions of hypochlorous acid free of chlorides or chlorine prepared by the solvent extraction of hypochlorous acid from an aqueous chlorination mixture may be employed. These solutions can be prepared, for example, by the process described in U.S. Pat. No. 3,578,400, issued to J. A. Wojtowicz et al.

In the process of the present invention, it is preferred to prepared hypochlorous acid by the reaction of an aqueous solution of an alkali metal hypochlorite with a chlorine containing compound. The hypochlorous acid may be prepared in situ or in a generator which is maintained at a temperature of from about 0° to about 5° C.

Hypochlorous acid of any convenient strength can be employed, for example, an aqueous solution containing from about 2 to about 20 percent by weight of HOCl. Preferably, a solution containing from about 5 to about 10 percent, and more preferably from about 6 to about 8 percent by weight of HOCl is used.

In the process of the present invention, ammelide and ammeline are believed to react with hypochlorous acid to produce a reaction mixture containing trichloroisocyanuric acid according to the following equations:

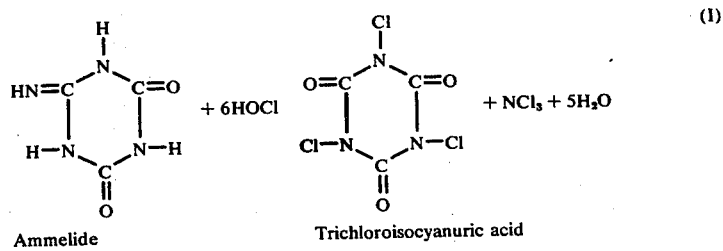

(1)

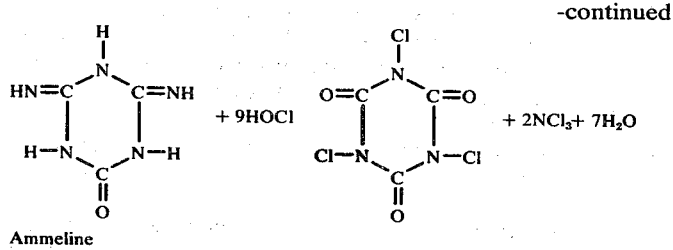

Ammeline

In the above equations, ammeline and ammelide are presented in the imino form, but the process of the present invention is applicable to all of the isomeric forms of these compounds.

The reaction between hypochlorous acid and the selected symmetrical triazine compounds is generally carried out using at least stoichiometric amounts of reactants. The stoichiometric amount of HOCl required is represented by the formula X + 2Y, wherein X represents the number of hydrogen and alkali metal atoms present in the triazine compound, and Y represents the number of nitrogen atoms in the triazine compound which are replaced by oxygen atoms. For example, ammelide, having 4 hydrogen atoms and 1 nitrogen atom, the imino group nitrogen atom, which is replaced by an oxygen atom, requires at least 6 moles of hypochlorous acid, a shown in Equation (I) above. Trichloroammelide, having 2 hydrogen atoms and 1 nitrogen atom which is replaced by oxygen, requires at least 4 moles of HOCl. Similarly, ammeline having 5 hydrogen atoms and 2 nitrogen atoms which are replaced by oxygen requires at least 9 moles of HOCl, as shown by Equation (II) above.

It is preferred to use an excess of HOCl above the stoichiometric amount, for example, from about 2 to about 80 and preferably from about 5 to about 60 mole percent.

Where less than stoichiometric amounts of HOCl are used, a reaction product which is a mixture of trichloroisocyanuric acid and chlorosubstituted ammelides or ammelines is obtained.

The process of the present invention may be carried out at reaction temperatures of from about −5° to about 50° C. with temperatures of from about 0° to about 25° C. being preferred.

During the reaction the pH of the reaction mixture is maintained at from about 2.5 to about 5.0, and preferably at from about 3.0 to about 4.5.

The selected symmetrical triazine compounds of the present invention are preferably reacted as an aqueous solution or aqueous slurry.

Gaseous nitrogen trichloride is formed during the reaction and its build-up in the reaction mixture should be avoided as it can be explosively dangerous.

To avoid this build-up it is possible, for example, to dilute the $NCl_3$ gas with an inert gas such as nitrogen.

In an additional embodiment, chlorine gas is fed to the reactor to remove nitrogen trichloride produced by sweeping it from the reactor. The gaseous mixture of $Cl_2$ and $NCl_3$ is then conducted to a scrubber unit containing an aqueous solution of an alkali metal compound, for example, an alkali metal hydroxide or an alkali metal carbonate. $NCl_3$ and $CL_2$ react with the alkali metal compound to form an aqueous solution of an alkali metal hypochlorite which may be further reacted, for example, with chlorine to produce hypochlorous acid.

In a further embodiment, a mixture of hypochlorous acid and chlorine may be used in place of hypochlorous acid alone in the process of the present invention. In the mixture, an amount of hypochlorous acid is required which is at least that required by the factor 2Y in the formula above and where chlorine may be present in amounts up to that required by the factor X. For example, in the production of trichloroisocyanuric acid from ammelide, a mixture comprising at least about 2 moles of hypochlorous acid and up to about 4 moles of $Cl_2$ may be used. Where the $Cl_2$ is used to remove the $NCl_3$ formed, it may be desirable to employ a small excess for this purpose.

Trichloroisocyanuric acid produced by the process of the present invention is easily separated from the reaction mixture, for example, by filtration.

The following examples are presented to further illustrate the invention without any intention of being limited thereby. All parts and percentages are by weight unless otherwise specified.

EXAMPLE 1

An aqueous slurry containing 0.0367 moles of ammelide was added to a reaction vessel. Hypochlorous acid (0.32 mole) was generated in situ by the reaction of chlorine gas with an aqueous solution of sodium hypochlorite containing 10.9 percent by weight of NaOCl. $Cl_2$ was added at a rate of about 0.5 parts per minute. The reaction was continued for about 2.42 hours with the reaction temperature being maintained in the range from about 8° to about 16° C and at a pH of about 4.2. During the reaction period, additional water was added to alleviate foaming. The reaction mixture was filtered and the wet cake washed with cold water. The wet cake was air dried and then oven dried at 100° C. for one hour. The dried product, 5.4 parts, had an available chlorine content of 91.5 percent and was identified by its infrared spectrum as being trichloroisocyanuric acid (theoretical available chlorine 91.5 percent) and was obtained in a yield of about 80 percent of theory based on the ammelide reacted. The mole ratio of HOCl employed to ammelide was 8.72:1.

EXAMPLE 2

The procedure of Example 1 was employed to react an aqueous slurry containing 0.0195 mole of ammeline. Hypochlorous acid (0.1828 mole) was produced in situ by the reaction of $CL_2$ with an aqueous solution containing 9.3 percent NaOCl. The reaction time was 150 minutes and 3.2 parts of the dried product was obtained having an available chlorine content of 88 percent. It was identified as trichloroisocyanuric acid by its infrared spectrum; yield, based on ammeline, was about 93 percent of theory. The mole ratio of HOCl to ammeline was 9.37:1.

EXAMPLE 3

To an overflow reactor vessel was added 0.385 mole of trichloroisocyanuric acid and 911 grams of a 7.35 percent NaCl solution. Hypochlorous acid was produced in a separate reactor by the reaction of chlorine with NaOCl. Over the reaction period of 70 minutes, 2.15 moles of a 7.4 percent aqueous solution of HOCl were fed at a uniform rate to the overflow reactor. Similarly fed to the reactor during the reaction period was an aqueous slurry consisting of 0.88 mole of monosodium cyanurate and 0.047 mole of the sodium salt of ammelide and 1.9 moles of chlorine gas. Of the HOCl supplied, about 1.8 moles reacted with the monosodium cyanurate and about 0.35 moles with the sodium ammelide. The reactor was externally cooled to maintain the temperature of about 13° C. and the reaction mixture was stirred. The reactor effluent was collected in a filter vessel and filtered intermittently to maintain a liquid level above the solid product. At the end of the reaction period, the reaction mixture was added to the filter vessel and the mother liquor drawn off. The product, dried in a forced-draft oven at 100° C. for one hour, had an available chlorine content of 91.4 percent and was obtained in a yield of 90.3 percent. Chromatographic and infrared analysis showed the product to be trichloroisocyanuric acid free of chlorinated ammeline.

EXAMPLE 4

The procedure of Example 3 was employed to react a mixture of 2.37 moles of HOCl and 2.1 moles of $Cl_2$ gas with an aqueous slurry containing 0.952 moles of monosodium cyanurate and 0.106 moles of ammeline. A 93.4 percent yield of trichloroisocyanuric acid was obtained having an available chlorine content of 91.5 percent. Chromatographic and infrared analysis showed the product having a trace (0.01 percent or less) of chlorinated ammeline.

What is claimed is:

1. A process for producing trichloroisocyanuric acid by the reaction of a symmetrical triazine compound selected from the group consisting of ammeline, chlorosubstituted ammeline, an alkaline, an alkali metal salt of ammeline, ammelide, chlorosubstituted ammelide, an alkali metal salt of ammelide, and mixtures thereof with hypochlorous acid to form a reaction mixture containing trichloroisocyanuric acid in which the number of moles of said hypochlorous acid reacted per mole of said symmetrical triazine compound is at least X + 2Y, where X represents the number of hydrogen and alkali metal atoms present in said symmetrical triazine compound and Y represents the number of nitrogen atoms in said symmetrical triazine compound which are replaced by oxygen atoms, and separating said trichloroisocyanuric acid from said reaction mixture.

2. The process of claim 1 in which the temperature of said reaction is maintained at from about −5° to about 50° C.

3. The process of claim 1 in which the pH of the reaction mixture is maintained at from about 2.5 to about 5.0.

4. The process of claim 1 in which said alkali metal is selected from the group consisting of lithium, sodium, potassium, cesium and rubidium.

5. The process of claim 1 in which said symmetrical triazine compound is selected from the group consisting of ammelide, chlorosubstituted ammelide, alkali metal salts of ammelide, and mixtures thereof, and Y is 1.

6. The process of claim 1 in which said symmetrical triazine compound is selected from the group consisting of ammeline, chlorosubstituted ammeline, an alkali metal salt of ammeline and mixtures thereof, and Y is 2.

7. The process of claim 5 in which said pH of said reaction mixture is maintained at from about 3.0 to about 4.5 and said reaction temperature is maintained at from about 0° to about 25° C.

8. The process of claim 7 in which said symmetrical triazine compound is ammelide.

9. The process of claim 7 in which said symmetrical triazine compound is a sodium salt of ammelide.

10. The process of claim 6 in which said pH of said reaction mixture is maintained at from about 3.0 to about 4.5 and said reaction temperature is maintained at from about 0° to about 25° C.

11. The process of claim 10 in which said symmetrical triazine compouund is ammeline.

12. A process for producing trichloroisocyanuric acid by the reaction of a symmetrical triazine compound selected from the group consisting of ammeline, chlorosubstituted ammeline, an alkali metal salt of ammeline, ammelide, chlorosubstituted ammelide, an alkali metal salt of ammelide, and mixtures thereof with a mixture of hypochlorous acid and chlorine to form reaction mixture containing said trichloroisocyanuric acid in which the number of moles of said hypochlorous acid and said chlorine per mole of said symmetrical triazine compound is at least X + 2Y, where X represents the number of hydrogen and alkali metal atoms present in said symmetrical triazine compound, where Y represents the number of nitrogen atoms in said symmetrical triazine compound which are replaced by oxygen atoms, and where said number of moles of said hypochlorous acid per mole of said symmetrical triazine compound is at least 2Y, and separating said trichloroisocyanuric acid from said reaction mixture.

13. The process of claim 5 in which the reaction temperature is maintained at from about −5° to about 50° C.

* * * * *